United States Patent
Chang

(10) Patent No.: US 6,368,317 B2
(45) Date of Patent: Apr. 9, 2002

(54) URETHRAL CATHETER AND URINARY DRAINAGE BAG ADAPTOR FOR PREVENTION OF NOSOCOMIAL URINARY TRACT INFECTION

(76) Inventor: Hau Hsien Chang, 2120 Truxtun Ave., Bakersfield, CA (US) 93301

( * ) Notice: Subject to any disclaimer, the term of this patent is extended or adjusted under 35 U.S.C. 154(b) by 0 days.

(21) Appl. No.: 09/134,413

(22) Filed: Aug. 13, 1998

Related U.S. Application Data

(63) Continuation-in-part of application No. 08/541,120, filed on Oct. 25, 1995, now abandoned, which is a continuation-in-part of application No. 08/011,511, filed on Feb. 1, 1993, now abandoned.

(51) Int. Cl.[7] .......................... A61M 27/00; A61M 1/00; B67D 5/64; B67D 5/40
(52) U.S. Cl. .................... 604/544; 222/133; 222/145.5; 222/444; 604/317; 604/327; 141/105
(58) Field of Search ............................... 607/82–83, 85, 607/89, 91, 32, 248; 222/133, 145.5, 444, 453; 141/9, 100, 105; 604/905, 544, 317, 377

(56) References Cited

U.S. PATENT DOCUMENTS

| | | | |
|---|---|---|---|
| 1,479,103 A | * | 1/1924 | Lyons |
| 2,901,149 A | * | 8/1959 | Richter |
| 4,209,013 A | | 6/1980 | Alexander et al. .......... 128/213 |
| 4,293,083 A | * | 10/1981 | Meares, Jr. |
| 4,738,668 A | | 4/1988 | Bellotti et al. .............. 604/283 |
| 4,773,901 A | | 9/1988 | Norton ........................ 604/265 |
| 4,810,241 A | | 3/1989 | Rogers ......................... 604/28 |
| 5,486,478 A | * | 1/1996 | Kuriyama ................... 601/248 |

* cited by examiner

Primary Examiner—John G. Weiss
Assistant Examiner—K. M. Reichle
(74) Attorney, Agent, or Firm—Townsend and Townsend and Crew, LLP

(57) ABSTRACT

An urethral catheter and urinary drainage bag adaptor which includes a substantially cylindrical segment telescoping over a smaller diameter but longer substantially cylindrical segment. Both ends of the longer segment are open and both ends of the shorter segment are closed. Each segment also has a wall and a lumen. The longer segment includes a first portion, a shorter second portion and a substantially spherical-shaped third portion located between the other two portions. A storage chamber for antiseptics is defined by a closed space between the two segments and communicates with the lumen of the longer segment through at least one fenestration located on a wall of the third portion. The longer segment is a conduit for body fluid. A rotary valve is located in the third portion for controlling drainage of body fluids and collecting antiseptics from the chamber. The device allows draining body fluid to mix with a small aliquot of antiseptic collected from the chamber by a rotary valve to prevent ascending infection of the urinary tract without fluxing of the antiseptic into the body.

9 Claims, 7 Drawing Sheets

URETHRAL CATHETER AND URINARY DRAINAGE BAG ADAPTOR FOR PREVENTION OF NOSOCOMIAL URINARY TRACT INFECTION

This is a continuation-in-part of, and claims the benefit of priority from U.S. patent application Ser. No. 08/541,120, filed on Oct. 25, 1995, which was a continuation-in-part of U.S. patent application Ser. No. 08/011,511, filed on Feb. 1, 1993, both now abandoned. The full disclosures of each of these applications are hereby incorporated herein by reference.

BACKGROUND OF THE INVENTION

1. Field of the Invention

The invention relates to an adaptor that can be mounted between an end of an indwelling urethral catheter and a connector to an urinary drainage bag to prevent or reduce the incidence of urinary tract infection in a patient who needs to wear an indwelling urethral catheter during the course of the medical treatment.

2. Description of the Prior Art

Indwelling urethral catheterization in a closet drainage system is the standard of care in present day modern medical care for a patient who has bladder neck obstruction such as benign prostatic hypertrophy, or urinary incontinence such as neurogenic bladder, in surgery requiring perioperative urine output monitoring or for the patient being observed and treated in an intensive care unit requiring close urine output monitoring. Nosocomial urinary tract infection invariably develops within one week after a FOLEY catheter, i.e. an urethral catheter with a retention balloon at one end, is left indwelling. Ascending infection by microorganisms through a lumen of the urethral catheter is thought to be one of the causes of nosocomial urinary tract infection. Conventional treatments include oral and intravenous antimicrobial therapy and intermittent irrigation of the urethral catheter with antibiotics and acetic acid solution. The treatments frequently fail to eradicate and control the urinary tract infection. Resistant strains of microorganisms frequently supersede, rendering the subsequent treatment more difficult and expensive and mortality hence increases.

SUMMARY OF THE INVENTION

The present invention provides apparatus and methods for connecting and reconnecting catheters, such as indwelling catheters, and in particular FOLEY urinary drainage catheters, from and to drainage bags and other external reservoirs, collection devices and the like. In particular, the present invention significantly reduces the risk of infection when an indwelling catheter is disconnected from and reconnected to a series of external collection devices of the type just mentioned. In the exemplary embodiments, the present invention provides for introducing an antiseptic material to the region where the catheter is being disconnected as an automatic part of the disconnection/reconnection procedure. That is, the system user need take no steps other than disconnecting and reconnecting the indwelling catheter to the external device, whereby the present invention automatically dispenses an antiseptic material to reduce the risk of infection. Although particularly suitable for use with FOLEY catheters, the present invention will also find use with other indwelling and transcutaneous catheters, such as implanted catheters used for exchanging dialysate with peritoneal catheters for ambulatory peritoneal dialysis.

Apparatus according to the present invention comprises an adaptor for connecting the end of the catheter, typically an indwelling FOLEY catheter as described above, to a connector on a collection bag, typically a urinary collection bag in the case of a FOLEY catheter. The adaptor comprises an adaptor body having a flow passage therethrough with a first connector at one end of the flow passage and a second connector at the other end of the flow passage. The first connector is adapted to removably connect a catheter, typically a proximal hub or other connector on a FOLEY catheter and to receive fluid from the connected catheter. The second connector is adapted removably connect and attach to the collection bag or other external device. A chamber which holds a liquid antiseptic is further provided, typically being part of the adaptor body, preferably being disposed annularly about the adaptor body. A valve is included in the flow passage and has a first position where the flow passage is open and a second position where the flow passage is closed. The valve has a valve passage which receives a dose of the antiseptic material from the chamber each time the valve is closed and releases the dose of antiseptic material into the flow passage each time the valve is opened. In this way, each time the user turns off the valve to disconnect the urinary collection bag or other device, a dose of the antiseptic will automatically be collected in the passage of the valve mechanism. Then, after the collection bag is reconnected, the valve is opened and the valve passage automatically releases the antiseptic into the flow path between the indwelling catheter and the collection bag. The release of antiseptic will greatly reduce the risk of infection becoming established and travelling up the indwelling catheter to harm the patient.

In the exemplary embodiments, the valve comprises a rotary plug having the flow passage therein. The plug may be rotated so that the valve passage is in alignment with the flow passage in the adaptor body in order to open the valve. Similarly, the valve may be rotated so that the valve passage is out-of-alignment with the flow passage in the adaptor body in order to close the valve. With such configuration, the antiseptic material may be conveniently dispensed by providing openings between the chamber holding the antiseptic and the rotary plug, where the openings are positioned in the adaptor body so that fluid flows into the valve passage each time the valve is closed and the valve passage falls out of alignment with the flow passage. In one exemplary embodiment, the plug rotates about an axis which is perpendicular to the valve passage. In another embodiment, the plug rotates about an axis parallel to but spaced laterally apart from the valve passage.

The present invention further comprises methods for inhibiting infection of an indwelling catheter, such as a FOLEY urinary drainage catheter. The catheters are connected to a receptacle, usually a drainage bag, and a valve is provided in a connecting line to isolate the proximal end of the indwelling catheter when it is desired to remove one drainage bag and replace it with an empty drainage bag or other receptacle. The method comprises closing the valve between the indwelling catheter and the drainage receptacle and introducing a dose of antiseptic material into a valve passage of the closed valve. The drainage bag may then be disconnected and a new bag reconnected while the valve remains closed. When the valve is opened to reestablish a drainage path from the catheter to the drainage bag, the antiseptic material is automatically released through the valve and into the connecting line between the catheter and the drainage bag. As described above with respect to the device, such release of antiseptic material greatly reduces the risk of infection travelling up the indwelling catheter to the patient.

The antiseptic introducing step usually comprises positioning the valve passage to receive a dose from a chamber located adjacent the valve, typically located annularly about the valve an flow passage in the adaptor. Usually, the valve will be positioned to receive antiseptic each time it is closed and further positioned to release antiseptic to the indwelling catheter and/or the drainage bag each time the valve is opened. The volume of antiseptic material released will typically be in the range from 0.1 ml to 10 ml, and suitable antiseptic materials include betadine, acetic acid solution, hydrogen peroxide, and the like. It will also be possible to use antibiotics in place of or in combination with antiseptic agents.

DESCRIPTION OF THE PREFERRED EMBODIMENT

Figure 1:
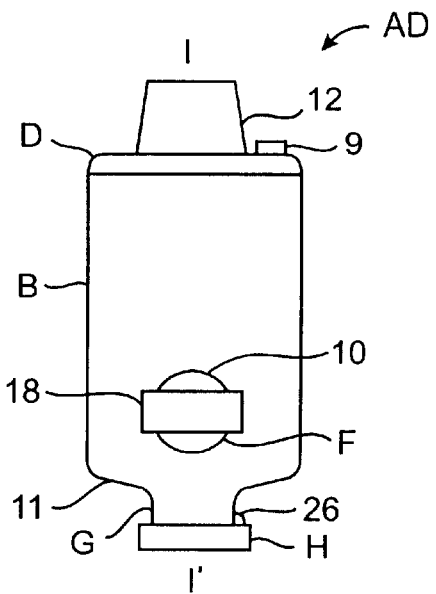
FIG. 1 is the front external view of the urethral catheter and urinary drainage bag adaptor.
Figure 2:
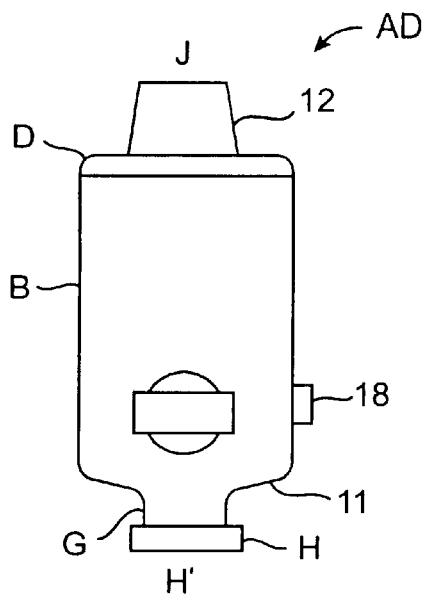
FIG. 2 is the side external view of the urethral catheter and urinary drainage bag adaptor.

The invention is an urethral catheter and urinary drainage bag adaptor for preventing nosocomial urinary tract infection. The adaptor comprises a body including first, substantially cylindrical segment having a length, a diameter, a wall, an axis and opposite open ends. One of the ends is adapted to receive body fluids from a discharge end of an indwelling urethral catheter or a discharge spigot of an urinary drainage bag and the other of the ends is adapted to discharge the body fluids. The first segment further has a first portion adjacent the one of the ends, a second portion adjacent the other of the ends and a third portion interposed between the first and second portions. The first portion has a length, a constant diameter lumen and a side wall. The second portion has a length shorter than the length of the first portion, a lumen having a diameter and a side wall. The third portion has a lumen. The third portion and the lumen thereof being spherically-shaped. The third portion and the lumen thereof having diameters which are larger than diameters of the first and second portions and the diameters of their respective lumens, respectively. The third portion further has a wall, a circular opening through the wall which opening has an axis, and at least one fenestration through the wall in at least one of an upper or lower hemispherically-shaped portion of the third portion. The lumen of the third portion fluidically communicates with the lumens of the first and second portions so as to define a lumen of the first segment.

The adaptor further comprises a second, substantially cylindrical segment having a length shorter than the length of the first segment, a diameter larger than the diameter of the first segment, a side wall, an axis, a first open end adjacent the first portion, a second end opposite the first open end and adjacent the second portion and a circular opening through the side wall which opening has an axis. The second segment surrounds, is spaced from and concentric with the first segment. The axes of the circular openings of the second segment and the third portion are aligned with each other but at right angles to the axes of the first and second segments. The second end of the second segment has an external diameter which tapers toward and to an exterior of the side wall of the second portion where the second end is fused thereto.

The adaptor still further comprises a third, substantially cylindrical segment connecting the circular openings of the second segment and the third portion. The third segment has a longitudinal axis at a right angle to the axes of the first and second segments, a lumen having a diameter no greater than the diameter of the lumen of the third portion, a wall and a circumferential groove on an interior surface of a midsection of the wall.

The adaptor includes a waterproof cover enclosing the first open end of the second segment. The first portion is sealingly received through a large central opening of the cover. A chamber is defined by and between the first segment, the second segment and the cover. The chamber is adapted to store antiseptics. The cover further has a small opening at a peripheral portion covered by a rubber seal. The small opening and the seal define an injection port adapted for refilling the chamber with antiseptics. The second segment and cover enclose the third portion. There is at least one fenestration which directly fluidically communicates with the chamber.

A substantially drumstick-shaped rotary valve is specially designed for controlling movement of the body fluids through the adaptor, i.e., is the key portion of the invention.

The valve comprises a substantially spherical portion located within the third portion and a handle portion extending from the spherical portion through the lumen of the third segment. The substantially spherical portion has an external diameter slightly smaller than the diameter of the lumen of the third portion, a side wall and a constant diameter lumen. The constant diameter lumen of the spherical portion has a diameter no greater in size than the diameters of the lumens of the first and second portions, opposite open ends and an axis which is coplanar with axes of the first, second and third portions. The handle portion comprises a substantially column-shaped stick having an end connected to a midportion of an exterior surface of the side wall of the spherical portion, a length greater than a length of the third segment, a cross-sectional diameter smaller than the diameter of the lumen of the third segment, an axis at a right angle to the axis of the lumen of the spherical portion, a wall and a circumferential groove on an exterior surface of a midsection of the wall of the handle.

A fourth, substantially cylindrical segment fills a space in the lumen between the wall of the third segment and the wall of the stick to prevent fluid leakage. The fourth segment has a length the same as the length of the third segment, a concave-shaped open end facing the spherical portion of the rotary valve, an opposite linear-shaped open end, a wall having a circumferential protrusion on a midportion of each of inner and outer surfaces thereof received in the grooves of the stick and third segment, respectively, and an axis coaxial with the axis of the third segment but perpendicular to the axes of the first and second segments.

In order to protect the second end from external contamination a fifth, substantially cylindrical segment is provided. The fifth segment has a lumen with a diameter larger than the external diameter of the second portion, a length longer than a length of a part of the second portion projecting from the fused second end of the second segment and extending to the other of the ends of said first segment, an axis coaxial with the axes of the first and second segments, a wall spaced from and concentric with the second portion so as to encircle said part of the second portion and the other of the ends, a first end fused to the tapered diameter of the second segment and a second opposite end having a living hinge on one side and a male locking mechanism on an opposite side.

Finally, a circular cover having a diameter slightly larger than an external diameter of the fifth segment is provided. The cover has a rim, a female locking mechanism complementary to the male locking mechanism at one side of the rim and is connected to the living hinge on a side of the rim opposite to the one side so as to be anchored to the fifth segment.

The adaptor can be mounted to an end of a FOLEY catheter alone which catheter is placed in a patient's bladder. This combination allows an ambulatory patient who wears the catheter to do so without a urinary drainage bag if desired enabling freer ambulation. The adaptor may also be mounted to an outlet or discharge spigot of a urinary drainage bag or one adaptor may be mounted between the catheter and the urinary drainage bag above the bag and another adaptor may be mounted to the outlet or discharge spigot.

Once the adaptor is mounted, the rotary valve is turned in one direction until the axis of the lumen of the spherical portion is at a right angle to the lumens of the first and second portions stopping any body fluid drainage through the first segment and preventing communication of prestored antiseptics in the chamber with the lumen of the spherical portion via the at least one fenestration. The valve is further turned in the one direction until the lumen of the spherical portion is aligned with the at least one fenestration permitting a small aliquot of antiseptics to drain through the at least one fenestration from the chamber and collect in the lumen of the third portion. Finally, the valve is turned further in one direction to align the lumen of the spherical portion with the first and second portions of the first segment allowing drainage of body fluids again. As the body fluid drains through the first segment, the body fluid mixes with the antiseptic in the lumen of the spherical portion prior to being discharged from the other end of the first segment. The bactericidal effect of the antiseptic prevents or reduces the incidence of ascending urinary tract infection in a patient who wears an indwelling catheter with the present adaptor for a prolonged period of time, for example, in a closed body fluid drainage system. Furthermore, the lumen of the spherical portion does not fluidically communicate with the lumens of the first and second portions and the at least one fenestration simultaneously. Thus, unlike the prior art, the rotary valve prevents antiseptic from fluxing into the body cavity by providing only intermittent contact of the draining body fluids with a small quantity of antiseptics rather than continuous unrestricted contact with the body fluids and body cavity.

The invention may include structural modifications in order to enforce the sterile condition of the lumen of the first segment as well as to prevent flux of antiseptics in the chamber to the lumen of the first portion. These modifications include the provision of an additional rotary valve in an additional spherically-shaped portion located between the one of the ends of the first segment and the first rotary valve and the third portion, an eccentrically located lumen in the spherical portion and the at least one fenestration located in the lower hemispherically-shaped portion of the third portion.

The invention may also include at least one fenestration in the wall of both the upper and lower hemispherically-shaped portion and the at least one fenestration being coplanar with the axis of the lumen of the spherical portion of the rotary valve. The adaptor may also be formed of non-biohazardous material.

Figure 3:
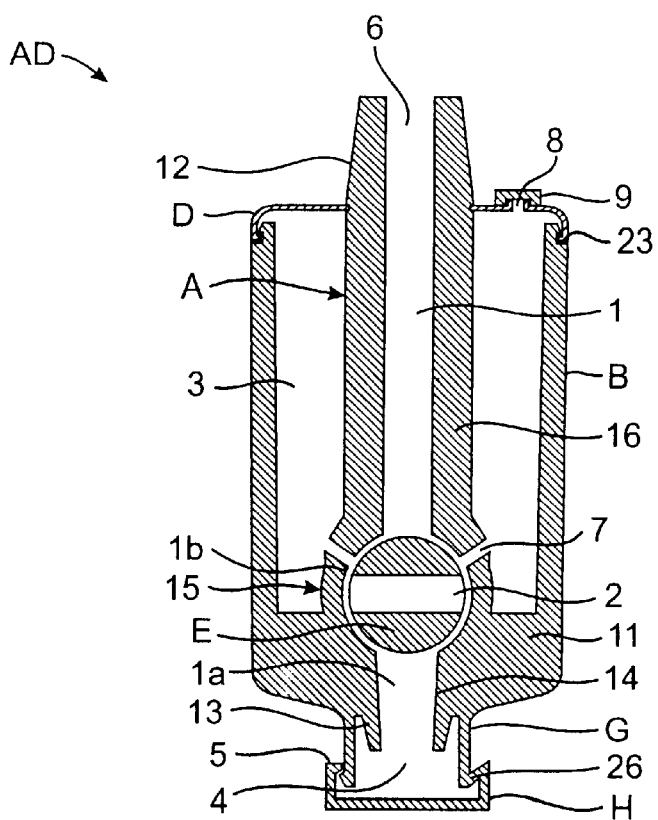
FIG. 3 is a longitudinal cross-sectional view of the adaptor taken along line J–J' in FIG. 2.
Figure 4:
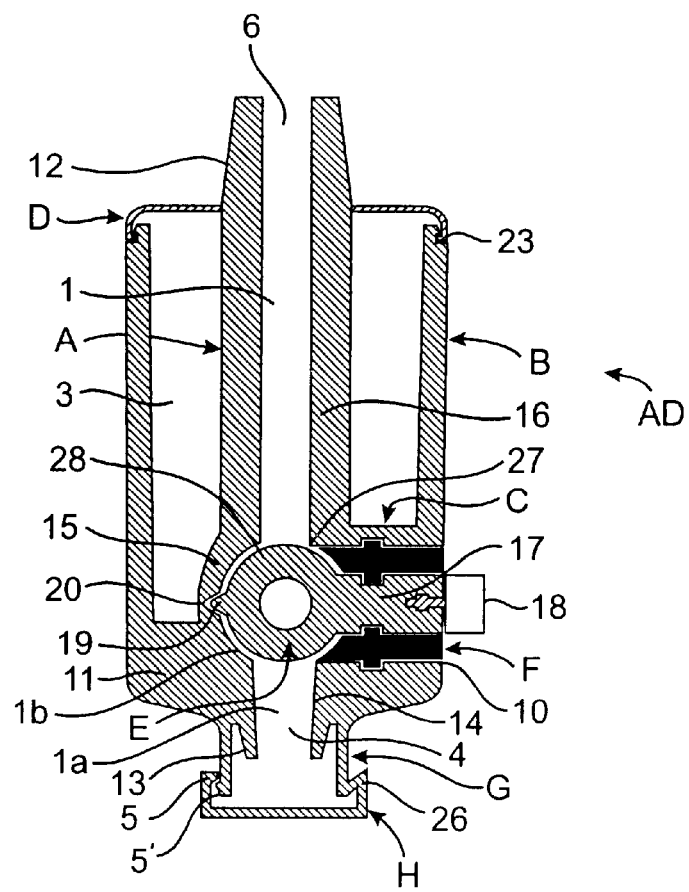
FIG. 4 is a longitudinal cross-sectional view of the adaptor taken along line I–I' in FIG. 1.

Referring to FIGS. 1, 2, 3 and 4 an embodiment of the urethral catheter and urinary drainage bag adaptor AD for the prevention of nosocomial urinary tract infection is illustrated. In these Figures the device consists of eight parts A–H. Part A (FIGS. 3 and 4) is a first, substantially cylindrical body or segment and is the longest segment of the adaptor. It is comprised of three parts: a longer first portion 16, a second shorter portion 14 and a spherically-shaped third portion 15. The third portion is interposed between the first and second portions. The first and second portions have lumens 1, 1a, respectively and the third portion has a lumen 1b which is spherically-shaped and larger in diameter than the lumens 1, 1a. The first portion 16 has one open end 6 adapted to receive body fluids, e.g., urine from the discharge of an indwelling urethral catheter or a discharge end or spigot of an urinary drainage bag. Another opposite open end 4 is adapted to discharge body fluids and a circular opening 27 is formed through a wall of the third portion. There is at least one opening or fenestration 7 through a wall in at least one of a upper hemisphere or a lower hemisphere of the third portion 15 of cylindrical segment A. There is a small recess 20 in an interior surface of the wall of the third portion 15 opposite to the circular opening 27 to accommodate a pointed projection 19 at a tip of a rotary valve E. The diameters of the first and second portions of the first segment are the same as a diameter of a lumen of a tapered open end or discharge of the catheter, a urinary drainage bag tubing and the urinary drainage bag discharge end or spigot. The lumen of the third portion 15 houses a substantially spherical portion of the rotary valve E. Referring to FIGS. 3 and 4, the external diameter of the first and second portions 16, 14 taper toward the ends 6,4, respectively.

Figure 5:
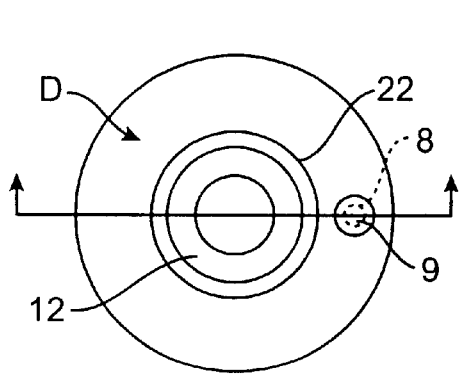
FIG. 5 is a top view of the urethral catheter and urinary drainage bag adaptor.
Figure 6:
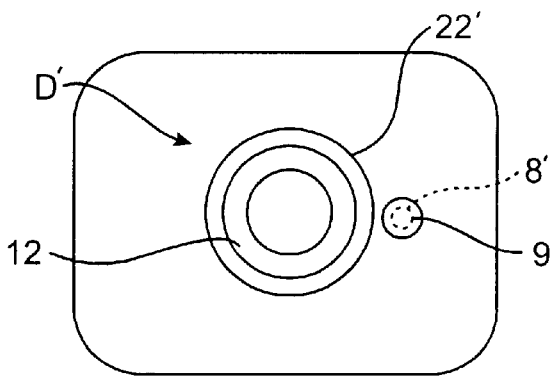
FIG. 6 is a top view of another embodiment of the adaptor.
Figure 7:
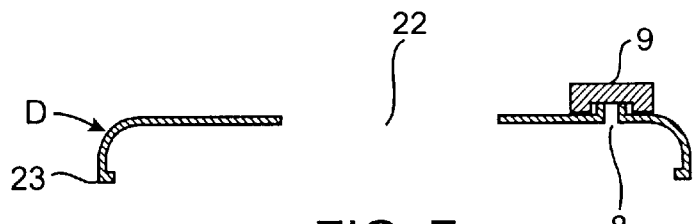
FIG. 7 is a longitudinal cross-sectional view of the cap taken along line K–K' in FIG. 5.

The second, substantially cylindrical segment B, see FIGS. 1 and 3–4, comprises a diameter which is constant throughout most of the segment. The external configuration is variable and can be circular, FIG. 5 or rectangular, FIG. 6. The second segment B is larger in diameter and shorter in length than the first segment A. It telescopes over the first segment A including the third portion and defines a space 3 with the wall of the first segment A. The space 3 adjacent one end of the second segment is sequestered by a cover D with the center of the cover being cut out to accommodate the one end 6 of the first segment. Cover is a round D or rectangular-shaped D' plate with a large central opening 22, 22' and a smaller eccentric opening 8, 8'. It has a L-shaped waterproof seal 23 at the peripheral edge. The central opening accommodates the first segment. Again the junction of the edges of the two elements is waterproof. Portion 12 is the portion of the first portion external of the cover D, D'. The smaller eccentric opening 8, 8' is covered by a rubber seal. It is used as an injection port for antiseptic solutions. A second end of the second segment adjacent the other end 4 of the first segment has an external diameter which tapers toward the exterior of the side wall of the second portion where the second end is fused thereto. This tapered and fused second end is denoted 11 in FIG. 4. The cover D is of the same size and shape as the tapered and fused second end. There is a circular opening 10 in the wall of the second segment. The size of the opening 10 is the same as that of the side opening 27 on the third portion of the first segment A. The opening 10 also aligns with the opening 27. Both openings are connected together by a third, substantially cylindrical segment C. The space 3 is a storage space for the antiseptics. The space 3 communicates with the lumen of the rotary valve and the lumen of the third portion through the at least one fenestration 7.

Figure 8:
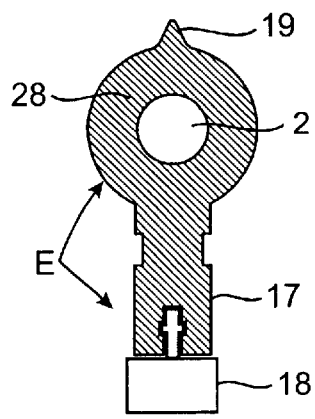
FIG. 8 is a transverse cross-sectional view of a rotary valve when a lumen of a spherical portion of the valve is in a "draining" or "vertical" position.
Figure 9:
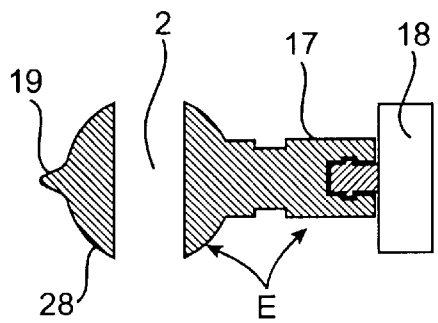
FIG. 9 is a longitudinal cross-sectional view of a rotary valve when a lumen of a is in a "draining" or "vertical" position.
Figure 14:
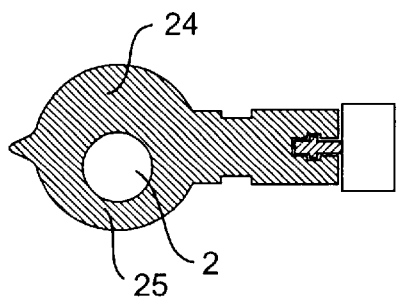
FIG. 14 is a transverse cross-sectional view of another embodiment of a rotary valve.
Figure 15:
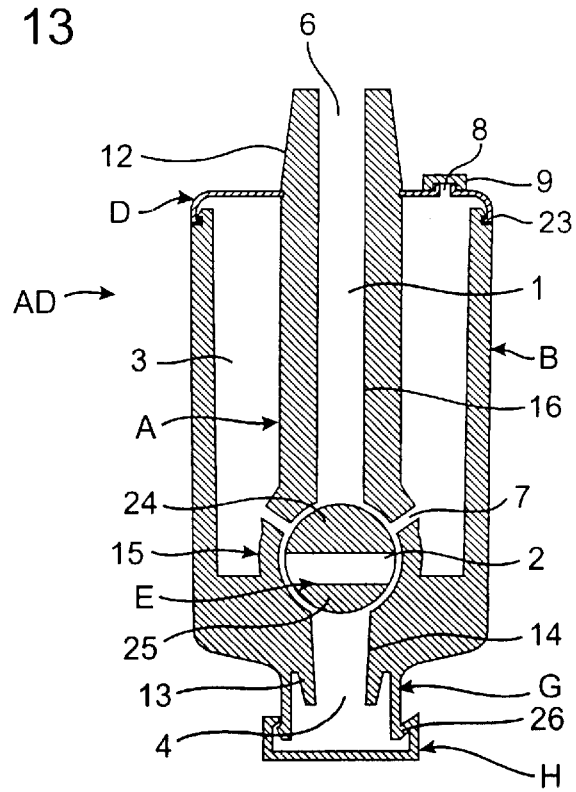
FIG. 15 is a longitudinal cross-sectional view of an adaptor taken along J–J' of FIG. 2 but with the rotary valve of FIG. 14.

Referring to FIGS. 1, 3–4, 8–9, 14 and 15, part E is a rotary valve of the adaptor. It comprises a substantially-spherical portion 28 having a straight tubular lumen 2, a long handle 17 extending from a side wall of the spherical portion, an extension 18 of the handle of the rotary valve to outside of the second segment for manual manipulation; A pointed protrusion or projection 19 from the middle of the sidewall or tip of the rotary valve opposite to the point on the side of the wall where the handle is attached for providing, with recess 20, stabilization of the spherical portion of the rotary valve within the lumen of the third portion. The axis of the lumen 2 is at a right angle with an axis of the handle 17 of the rotary valve. The spherical portion 28 of the rotary valve resides in the lumen of the third portion, whereas the handle 17 of the rotary valve lies within the lumen of the third segment C. The external diameter of the spherical portion of the rotary valve is slightly smaller than the diameter of the lumen of the spherical portion so that spherical portion 28 slides smoothly within the lumen of the third portion without fluid leakage. The handle 17 of the rotary valve comprises a solid column-shaped stick with a diameter smaller than the diameter of the third segment C. The space between the handle of the rotary valve and the wall of the third segment is filled with a fourth, substantially cylindrical segment F to prevent fluid leakage. The diameter of the lumen 2 of the spherical portion is the same as or slightly smaller than the diameters of the lumens of the first and second portions. The lumen 2 of the spherical portion can be located centrally as illustrated in FIGS. 8 and 9 or eccentrically located as illustrated in FIG. 14 and 15. In the latter case, one side of the wall 24 is thicker and heavier than the remainder of the wall 25. The eccentric position of the lumen also enforces the sterile condition of the lumen of the first segment as well as prevents the flux of the antiseptics in the chamber to the lumen of the first portion.

Referring to FIGS. 1 and 4, the fourth, substantially-cylindrical segment F is a water proof seal within the third segment C. The fourth segment fills the space between the handle 17 of the rotary valve and the wall of the third segment. It has the same length as the third segment extending from the side opening 27 to the side opening 10. The fourth segment has a concave-shaped open end facing the spherical portion of the valve and an opposite linear-shaped open end. The fourth segment also includes circumferential protrusions on a midportion of inner and outer surfaces thereof received in grooves of the handle and third portion, respectively. The third and fourth segments have axes coaxial with one another but perpendicular to the axes of the first and second segments.

Part G is a fifth, substantially-cylindrical segment. It comprises a segment with a lumen having a diameter larger than the external diameter of the first segment at end 4 and a length longer than a portion 13 of the second portion projecting from the tapered fused portion 11. The fifth segment telescopes over portion 13 and open end 4. A circular edge of one end of the fifth segment is fused with the tapered fused portion 11. The opposite open end projects beyond the open end 4. The fifth segment is the circular guard around the discharge end 4 of the first segment to protect it from external contamination.

Part H is a circular plate or cover with a diameter slightly larger than the external diameter of the fifth segment, one portion of the peripheral edge or rim of the cover has an inverted invert L shape female locking device 5 to engage a male locking device 5' on the opposite open end of the fifth segment. There is a living hinge 26 on the edge or rim of the cover opposite to the female locking device. The living hinge connects the cover to a point of the opposite open end of the fifth segment opposite to the male locking device.

Figure 16:
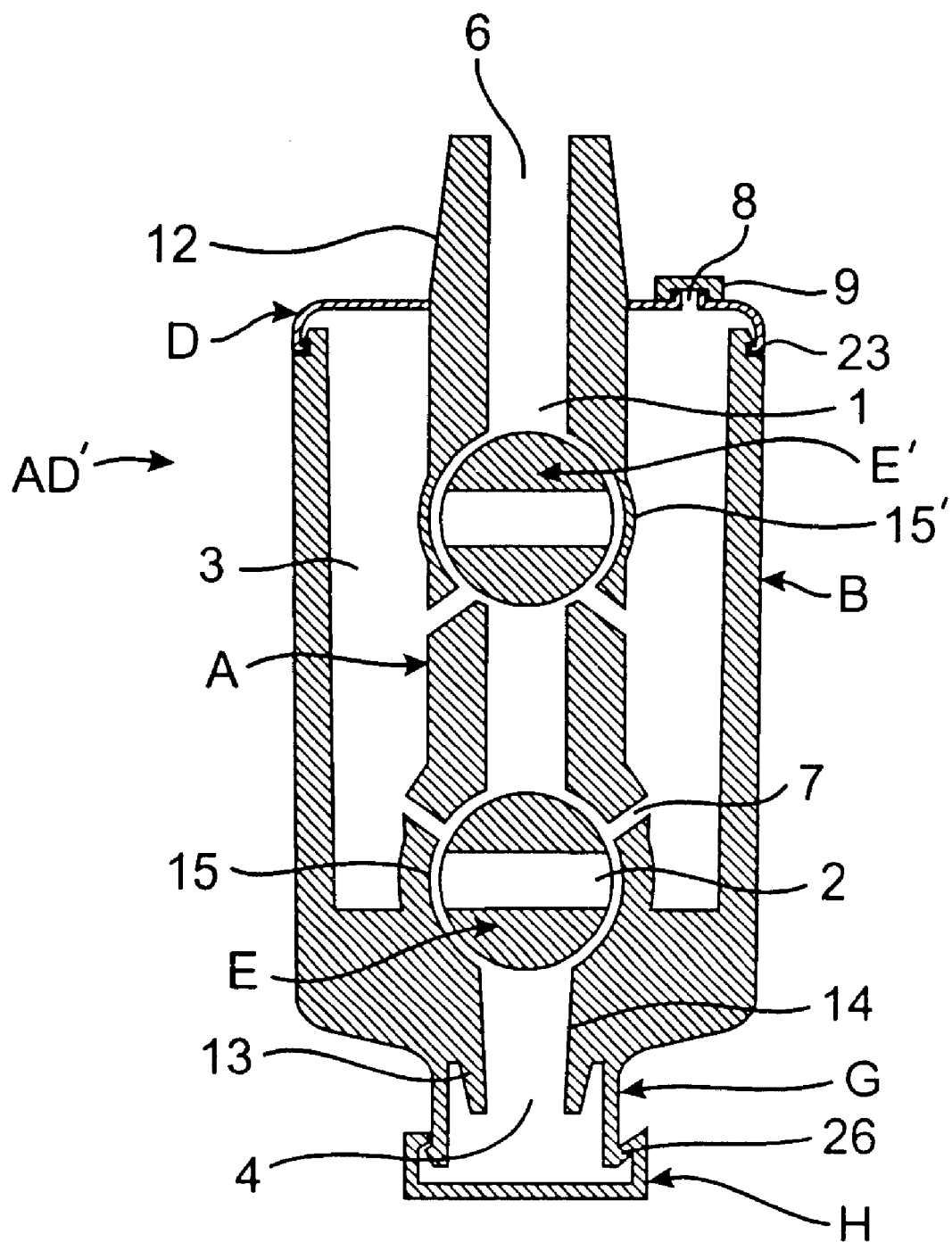
FIG. 16 is a longitudinal cross-sectional view of still another embodiment of an adaptor taken along a line similar to line J–J' in FIG. 2.

Referring to FIG. 16, a modified adaptor AD' is illustrated which includes a second rotary valve E' in a spherically-shaped portion and lumen 15' like the first rotary valve and third portion in the first segment. This structure also enforces the sterile condition of the lumen of the first segment as well as prevents flux of the antiseptics in the chamber 3 to the lumen of the first portion.

Figure 13:
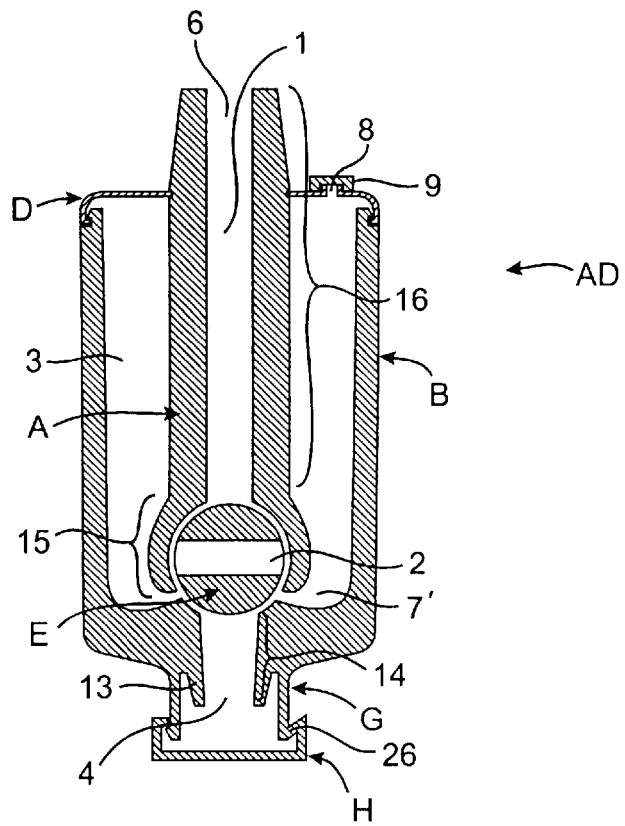
FIG. 13 is a longitudinal cross-sectional view of another embodiment of an adaptor taken along a line similar to line J–J' in FIG. 2.

Referring to FIGS. 3 and 13, the at least one fenestration 7' is shown on the lower hemispherical portion of the spherical portion. This structure also enforces the sterile condition of the lumen of the first segment as well as prevents flux of the antiseptics in the chamber 3 to the lumen of the first portion.

Figure 10:
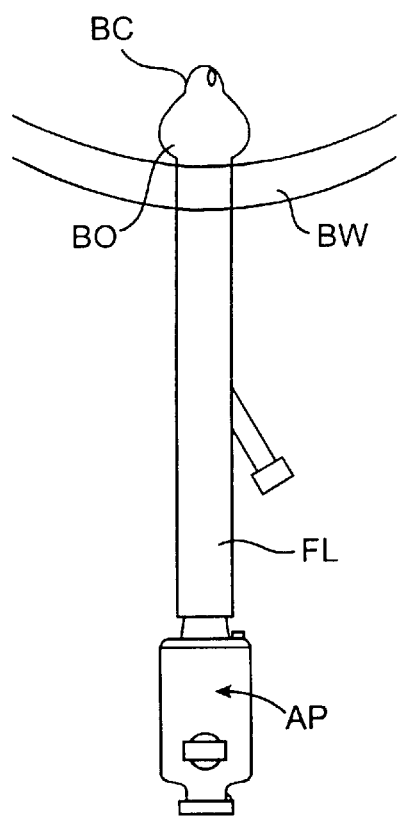
FIG. 10 is a schematic view of one clinical applications using an adaptor attached to a discharge end of a FOLEY catheter.

FIG. 10 illustrates a schematic view of one clinical applications in which BC denotes a urinary bladder cavity, BW denotes the bladder wall, BO represents the balloon of a FOLEY catheter FL and AP is the adaptor.

Figure 11:
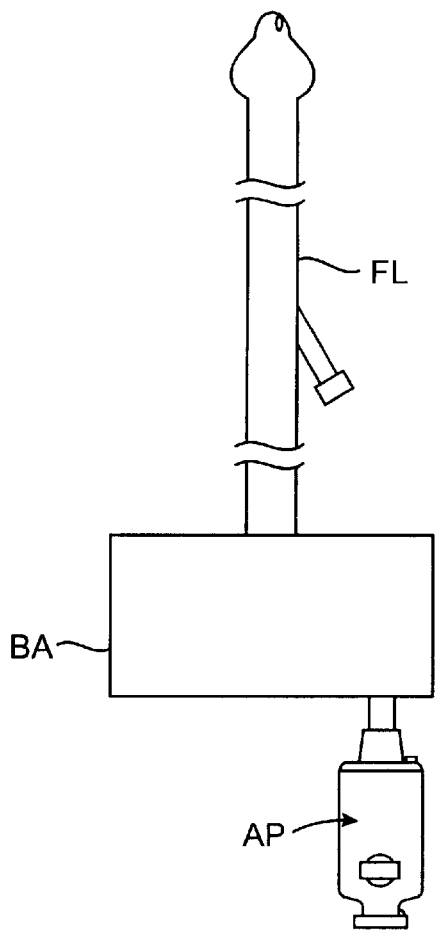
FIG. 11 is a schematic view of another clinical application using an adaptor attached to the discharge end or spigot of an urinary drainage bag.
Figure 12:
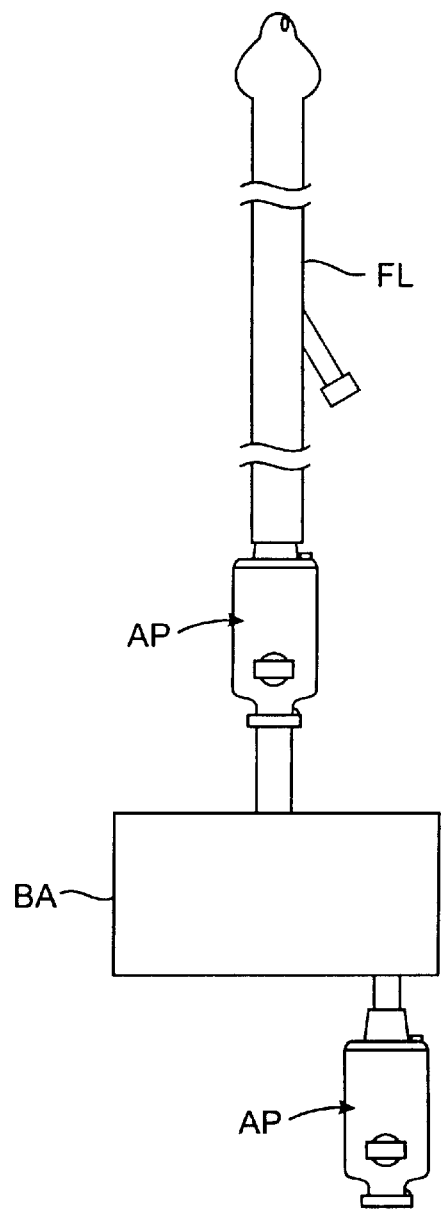
FIG. 12 is a schematic view of still another clinical applications using one adaptor attached between a "FOLEY" catheter and an urinary drainage bag and one adaptor attached to the discharge end or spigot of the urinary drainage bag.

FIGS. 11 and 12 illustrated schematic views of other clinical applications in which FL denotes a FOLEY catheter, BA denotes a urinary drainage bag and AP is the adaptor.

In the previous embodiments, the rotary valve plugs all rotated about an axis perpendicular to the valve passage in the plug. Such an orientation has the disadvantage that the peripheral surface of the plug which is exposed to the collected urine when the valve is closed, as shown in FIG. 3, can be turned to face the FOLEY or other indwelling catheter, thus increasing the risk of infection.

Figure 17:
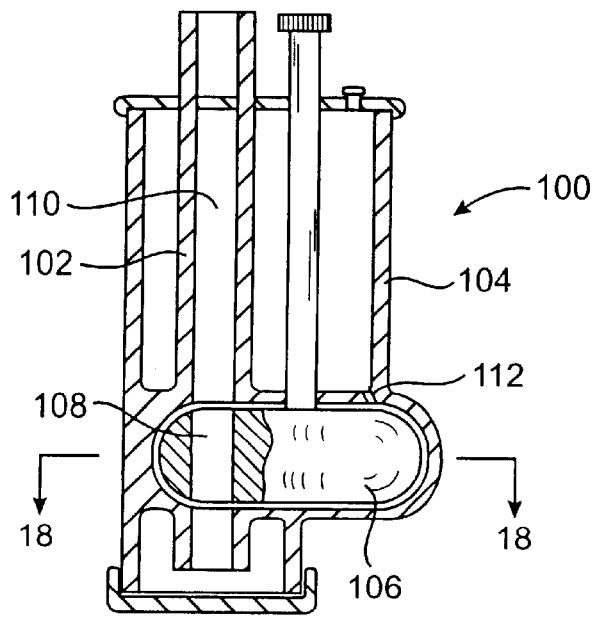
FIG. 17 is a side cross-sectional view of yet another embodiment of the valve of the present invention.
Figure 18:
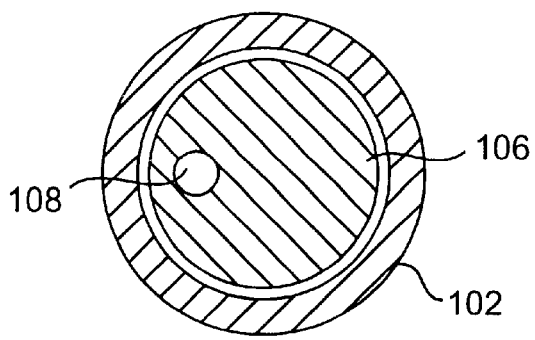
FIG. 18 is a cross-sectional view taken along line 18—18 of FIG. 17.
Figure 19:
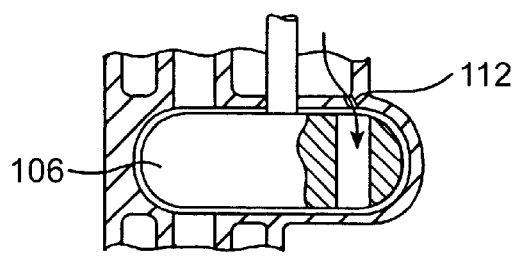
FIG. 19 is a partial cross-sectional view of the valve of FIGS. 17 and 18, shown with the valve closed in a position in which antiseptic fills the valve plug passage.

The valve embodiment of FIGS. 17–19 reduces the risk of such accidental infection by rotating the valve plug about an axis parallel to but spaced-apart from the valve passage in the plug. As shown in these Figs., a valve 100 including a body segment 102, a surrounding chamber 104 for holding an antiseptic material, and a rotary valve plug 106 having a valve passage 108 which may be aligned with a main lumen 110 in the body segment 102 (as shown in FIG. 17) or which may be rotated out-of-alignment, as shown in FIG. 19. Rotation is effected using a torque shaft FIG. 17. Antiseptic flows into the passage 108 when the valve is closed by moving the passage 108 beneath a opening 112 which permits the flow of the antiseptic from the chamber 104 to the valve passage 108. The rotary plug 106 may be manually turned using a torque member 114 which extends from the nominally upper surface of the plug 106.

A particular advantage of the design of FIGS. 17–19 is that the side of the valve plug 106 which is exposed to the urine collection side of the valve will never be directly exposed to the relatively clean patient side of the valve, thus reducing the risk of infection significantly.

Although detailed embodiments of the invention are illustrated in the drawings and previously described in detail. This invention contemplates any configuration, dimension, design and relationships of components which will function in a similar manner and which will provide the equivalent result.

What is claimed is:

1. An adaptor for connecting an end of a catheter to a connector on a collection receptacle, said adaptor comprising:
   an adaptor body having a flow passage therethrough, a first connector at one end of the flow passage for removably attaching a catheter to receive fluid therefrom, and a second connector at another end of the flow passage for removably attaching a collection receptacle;
   a chamber adapted to hold a liquid antiseptic material; and
   a valve in the flow passage having a first position where the flow passage is closed to prevent flow between the one end and other end and a second position where the flow passage is open between the one end and the other end, wherein the valve has a valve passage comprising a tubular lumen which extends across the valve from a first location on the valve's exterior surface to a second location on the valve's exterior surface which is diametrically opposed to said first location, the tubular lumen adapted for receiving and holding a dose of antiseptic material from the chamber when the valve is closed and releasing the dose into the flow passage when the valve is opened by aligning the tubular lumen with the flow passage so that the lumen is positioned entirely within the flow passage.

2. An adaptor as in claim 1, wherein the chamber is formed in the adaptor body and comprises a sealable port for filling the chamber with antiseptic material.

3. An adaptor as in claim 2, wherein the valve may be rotated so that the valve passage is in alignment with the flow passage of the body to open the valve and further rotated so that the valve passage is out of alignment with the flow passage to close the valve.

4. An adaptor as in claim 3, wherein there is at least one opening between the chamber and the valve, wherein said opening is positioned in the adaptor body to allow flow of antiseptic material into the valve passage when the valve is closed.

5. A method for inhibiting infection, said method comprising:
   providing an indwelling catheter connected to a collection receptacle by an adaptor in a connecting line, wherein the adaptor comprises:
   an adaptor body having a flow passage therethrough, a first connector at one end of the flow passage for removably attaching the catheter to receive fluid therefrom, and a second connector at another end of the flow passage for removably attaching the collection receptacle;
   a chamber adapted to hold a liquid antiseptic material; and
   a valve in the flow passage having a fist position where the flow passage is closed to prevent flow between the one end and other end and a second position where the flow passage is open between the one end and the other end, wherein the valve has a valve passage comprising a tubular lumen which extends across the valve from a first location on the valve's exterior surface to a second location on the valve's exterior surface which is diametrically opposed to said first location, the tubular lumen adapted for receiving and holding a dose of antiseptic material from the chamber when the valve is closed and releasing the dose into the flow passage when the valve is opened by aligning the tubular lumen with the flow passage so that the lumen is positioned entirely within the flow passage;
   closing the valve between the indwelling catheter and the collection receptacle;
   introducing a dose of antiseptic material into the valve passage while the valve is closed;
   disconnecting the collection receptacle and reconnecting a replacement collection receptacle; and
   opening the valve wherein the antiseptic material is released through the valve into the connecting line, whereby the risk, of infection of the indwelling catheter is reduced.

6. A method as in claim 5, wherein introducing the dose of antiseptic material comprises positioning the valve passage to receive the dose from the chamber adjacent the valve.

7. A method as in claim 6, wherein the valve is positioned to receive the antiseptic material each time it is closed and positioned to release the antiseptic material each time it is opened.

8. A method as in claim 5, wherein a volume of antiseptic material in the range from 0.1 ml to 10 ml is released.

9. A method as in claim 5, wherein the antiseptic material is betadine, acetic acid solution, or hydrogen peroxide.

* * * * *